United States Patent [19]
Wasserman

[11] Patent Number: 5,823,503
[45] Date of Patent: Oct. 20, 1998

[54] HANGER FOR HANGING AN INTRAVENOUS FEEDING BOTTLE

[75] Inventor: Thomas E. Wasserman, Avon lake, Ohio

[73] Assignee: Thomas Packaging Corporation, Avon Lake, Ohio

[21] Appl. No.: 701,107

[22] Filed: Aug. 21, 1996

[51] Int. Cl.[6] .................................................. A47G 29/00
[52] U.S. Cl. ....................................... 248/683; 248/205.3
[58] Field of Search .................................... 248/683, 682, 248/309.1, 317, 205.3

[56] References Cited

U.S. PATENT DOCUMENTS

| | | |
|---|---|---|
| 2,135,236 | 12/1938 | Koppelman . |
| 2,362,523 | 10/1944 | Armstrong, Jr. et al. . |
| 2,635,604 | 1/1953 | Fredrickson . |
| 3,231,919 | 2/1966 | MacDonald . |
| 3,387,732 | 6/1968 | Jellies .................................. 248/682 X |
| 3,635,367 | 1/1972 | Morita et al. . |
| 3,688,348 | 9/1972 | Klotz et al. ...................... 248/309.1 X |
| 3,744,658 | 7/1973 | Fujio . |
| 3,893,495 | 7/1975 | Standifer . |
| 4,460,143 | 7/1984 | Ohama . |
| 4,526,404 | 7/1985 | Vazquez . |
| 4,673,148 | 6/1987 | Oliver .............................. 248/309.1 X |
| 4,796,937 | 1/1989 | Andrea . |
| 4,832,301 | 5/1989 | Hiramoto et al. . |
| 4,902,547 | 2/1990 | Good .................................. 248/317 X |
| 4,934,646 | 6/1990 | Doyle .................................. 248/309.1 |
| 4,948,000 | 8/1990 | Grabenkort . |
| 5,135,125 | 8/1992 | Andel et al. ......................... 215/100 A |
| 5,490,658 | 2/1996 | Coward et al. .......................... 248/683 |

FOREIGN PATENT DOCUMENTS

| | | |
|---|---|---|
| 0140420 | 8/1985 | European Pat. Off. . |
| 0140420 | 8/1989 | European Pat. Off. . |
| 3631021 | 3/1988 | Germany . |

*Primary Examiner*—Peter M. Cuomo
*Assistant Examiner*—Stephen Vu
*Attorney, Agent, or Firm*—Tarolli, Sundheim, Covell, Tummino & Szabo

[57] ABSTRACT

A hanger for hanging an intravenous feeding bottle on a hook includes an attaching portion for encircling a portion of the bottle and having an adhesive for attaching the hanger to the bottle. A hanger portion is movable relative to the attaching portion from a first position in which the hanger portion also encircles a portion of the bottle to a second position in which the hanger portion is spaced from the bottle and engageable with the hook. The hanger portion and the attaching portion are portions of a single piece of film. The hanger portion has first and second end portions connected to the attaching portion and a linear edge extending between first and second edges of the attaching portion. The linear edge has a length greater than one-half a distance between the first and second edges of the attaching portion measured along the linear edge. The linear edge extends parallel to a linear edge of the attaching portion when the hanger portion is in the first position. The hanger portion has a terminal edge extending parallel to the linear edge and lying adjacent a base of the bottle when the hanger portion is in the first portion.

11 Claims, 3 Drawing Sheets

5,823,503

HANGER FOR HANGING AN INTRAVENOUS FEEDING BOTTLE

BACKGROUND OF THE INVENTION

The present invention relates to a hanger for hanging an intravenous feeding bottle.

U.S. Pat. No. 5,135,125 discloses a known hanger for hanging an intravenous feeding bottle. The hanger comprises a label for identifying the contents of the bottle and a handle for suspending the bottle from a hook. The handle is integral with the label and is defined in the label by a pair of die-cut lines. The die-cut lines extend circumferentially and axially about the bottle when the hanger is adhered to the bottle. The handle may be moved relative to the label to a bottle hanging position in which the handle engages a hook. When in the bottle hanging position, the hanger is still integral with the label which is secured to the bottle. Thus, the bottle hangs in position on the hook due to the hanger.

SUMMARY OF THE INVENTION

A hanger for hanging an intravenous feeding bottle on a hook includes an attaching portion for attaching the hanger to the bottle and a hanger portion. The attaching portion encircles a portion of the bottle and has suitable means, such as an adhesive, for attaching the hanger to the bottle. The hanger portion is movable relative to the attaching portion from a first position in which the hanger portion encircles a portion of the bottle to a second position in which the hanger portion is spaced from the bottle and engageable with the hook. The hanger portion and attaching portion are portions of a single piece of film. The hanger portion has first and second end portions integral with and thus connected to the attaching portion.

In accordance with a first feature of the present invention, the hanger portion has a linear edge which extends between first and second edges of the attaching portion. The linear edge has a length greater than one half the distance between the first and second edges of the attaching portion measured along the linear edge. The linear edge extends parallel to a linear edge of the attaching portion when the hanger portion is in the first position.

In accordance with another feature of the present invention, the hanger portion has a terminal edge which is parallel with the linear edge of the hanger portion and lies adjacent the base of the bottle when the hanger portion is in the first position.

In accordance with yet another feature of the present invention, the hanger portion has a surface extending from a first end portion to a second end portion of the hanger portion. The surface encircles and faces the bottle when the hanger portion is in the first position and is engageable with the hook when the hanger portion is in the second position. The surface has a substantially arcuate shape and faces the bottle along its entire length when the hanger portion is in the second position.

BRIEF DESCRIPTION OF THE DRAWINGS

The foregoing and other features of the present invention will become more apparent to one skilled in the art to which the present invention relates upon reading the following description of the present invention with reference to the accompanying drawings, wherein.

DESCRIPTION OF THE PREFERRED EMBODIMENTS

Figure 1:
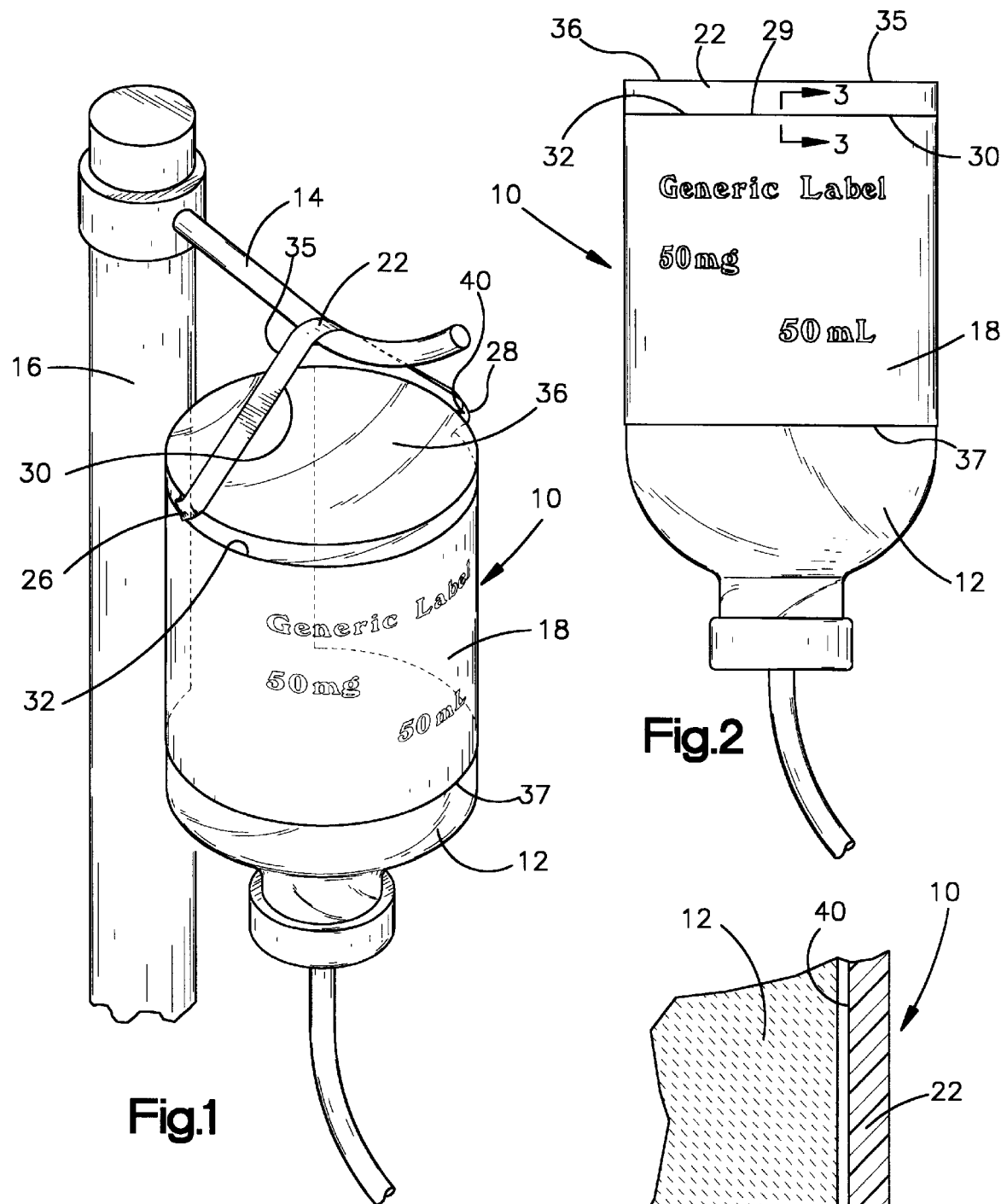
FIG. 1 is a pictorial view of an intravenous feeding bottle with a first embodiment of a hanger of the present invention attached to the bottle.

A first embodiment of the present invention includes a hanger 10 (FIG. 1) for hanging an intravenous feeding bottle 12 on a hook 14 of an intravenous stand 16. The hanger 10 is generally rectangular in shape and is preferably made of a single piece of film, such as 6.5 mil Valeron film, manufactured by Van Leer Flexibles, Inc. of Houston, Tex. The hanger 10 may be made of any suitable material, such as the Valeron film, plastic films, metal foil, etc.

The hanger 10 is attached to the bottle 12 by an attaching portion 18 of the hanger 10. The attaching portion 18 encircles a portion of the bottle. The attaching portion 18 has a layer of adhesive 20 (FIG. 3) for attaching the hanger 10 to the bottle 12. The attaching portion 18 (FIGS. 1 and 2) may have information about the contents of the bottle 12 printed on it in which case the hanger 10 would be a label.

Figure 2:
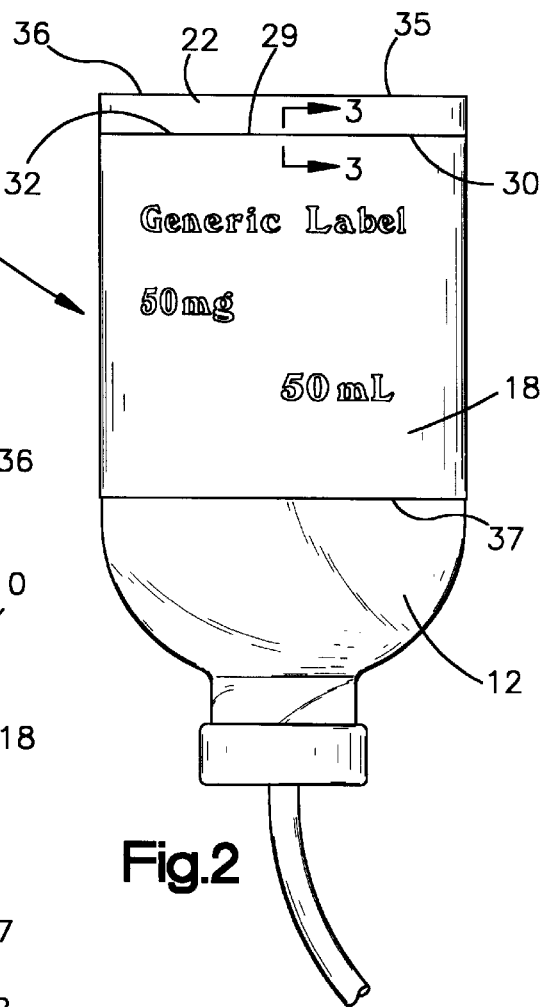
FIG. 2 is a plan view of the bottle of FIG. 1 with the hanger in a position engaging the bottle.

The hanger 10 also includes a hanger portion 22 for engaging the hook 14 to hang the bottle 12. The hanger portion 22 is movable from a first position in which the hanger portion also encircles a portion of the bottle 12 (FIG. 2) to a second position in which the hanger portion is spaced from the bottle and engageable with the hook 14 (FIG. 1).

Figure 4:
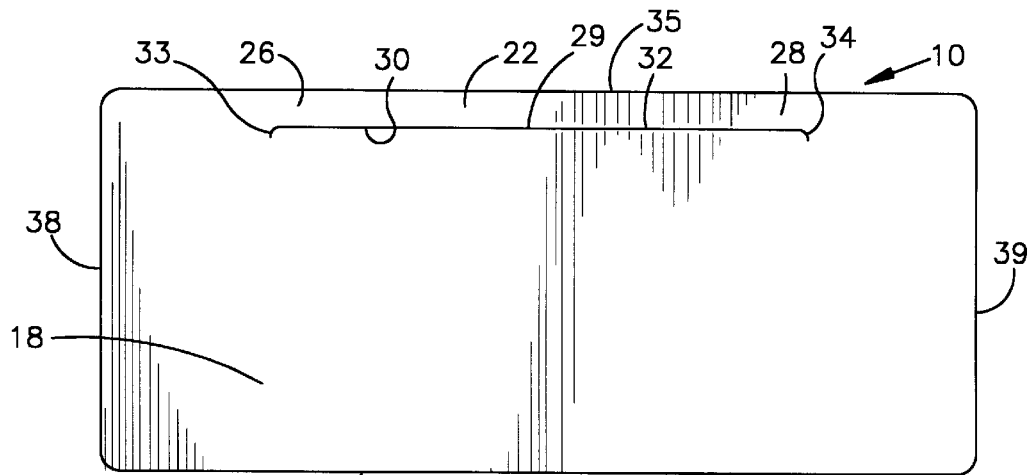
FIG. 4 is a plan view of the hanger of FIG. 1 detached from the bottle.

The hanger portion 22 has a first end portion 26 (FIG. 4) and a second end portion 28. The first and second end portions 26 and 28 are integral with and thus, connected to the attaching portion 18. The first and second end portions 26 and 28 are located on diametrically opposite sides of the bottle 12 so that the hanger portion 22 encircles approximately one half of the circumference of the bottle when the hanger portion is in the position shown in FIG. 2. The attaching portion 18 encircles more than one-half the circumference of the bottle. As shown in FIG. 1, the bottle 12 is round as viewed from the bottom and the hanger 10 is attached to a cylindrical surface of the bottle.

The hanger portion 22 is formed by a linear die-cut 29. The hanger portion 22 has a linear edge 30 (FIGS. 1–4) extending from the first end portion 26 to the second end portion 28. The linear edge 30 extends between edges 38 and 39 of the attaching portion 18 and has a length greater than one half the distance between the edges 38 and 39 measured along the linear edge 30. The linear edge 30 extends parallel to a linear edge 32 of the attaching portion 18 when the hanger portion is in the position shown in FIG. 2. The die-cut 29 has curved portions 33 and 34 (FIG. 4) adjacent end portions 26 and 28, respectively, to provide stress relief.

The hanger portion 22 has a terminal edge 35 (FIGS. 2 and 4) extending parallel to the linear edge 30. The terminal edge 35 lies adjacent to a base 36 of the bottle 12 when the hanger portion 22 is in the position shown in FIG. 2. Preferably, the terminal edge 35 lies in the plane of the base 36 of the bottle 12.

The attaching portion 18 has an edge 37 (FIG. 4) extending parallel to the edges 30, 32 and 35. The edges 38 and 39 of the attaching portion 18 extend parallel to each other and perpendicular to the edges 30, 32, 35, and 37. Accordingly, the hanger 10 has a generally rectangular shape.

Figure 3:
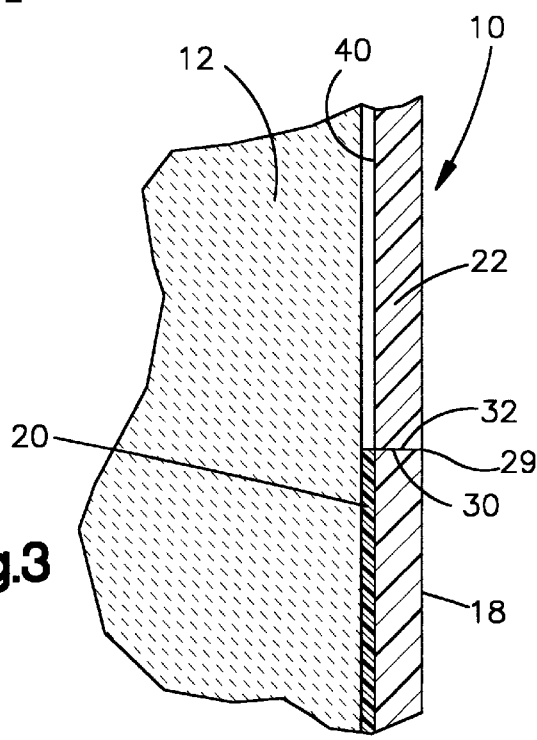
FIG. 3 is a sectional view taken generally along the line 3—3 of FIG. 2.

The hanger portion 22 includes a surface 40 (FIG. 3) extending from the first end portion 26 to the second end portion 28. The surface 40 does not have an adhesive layer and therefore, does not stick to the bottle 12. Alternatively, the surface 40 could have an adhesive which is suitably deadened, in a known manner, so as to not be effective. As shown in FIG. 3, a clearance may exist between the surface 40 of the hanger portion 22 if no adhesive is on the surface 40. The clearance is shown somewhat exaggerated in FIG. 3. The surface 40 encircles a portion of the bottle 12 and faces the bottle when the hanger portion 22 is in the position shown in FIG. 2. The surface 40 of the hanger portion 22 is engageable with the hook 14 when the hanger portion is in the position shown in FIG. 1. The surface 40 has a substantially arcuate shape and faces the bottle 12 along the entire length of the surface 40 when the hanger portion 22 is in the position shown in FIG. 1.

The movement of the hanger portion 22 from its first position to its second position is in the nature of a pivoting movement. The hanger portion 22 slides off of the bottle and pivots about its opposite connections to the attaching portion 18. Thus, the hanger portion 22 does not twist, and the surface 40 faces the bottle 12 along the entire length of the surface 40 when the hanger portion is in the position shown in FIG. 1.

Figure 5:
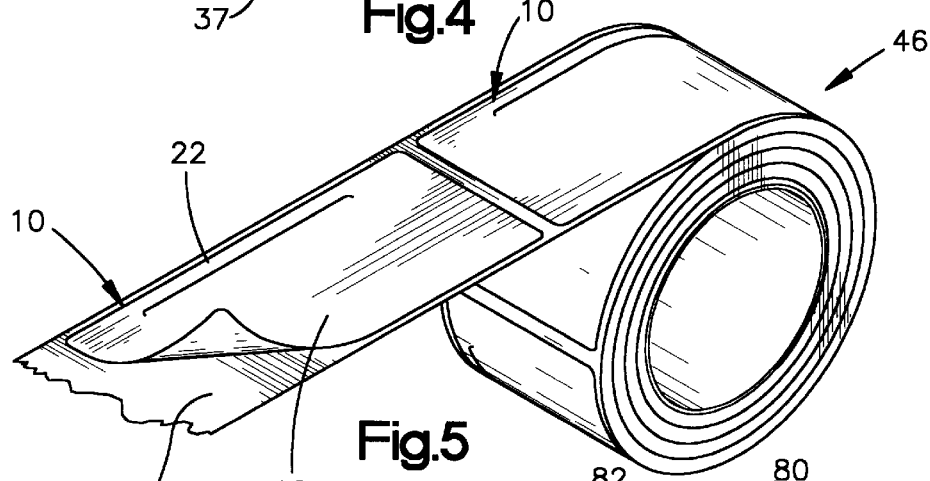
FIG. 5 is a pictorial view of a plurality of hangers on a roll.

It is contemplated that a plurality of hangers 10 may be supplied on a roll 46 (FIG. 5). The hangers 10 are provided on backing paper 48. The hangers 10 can be peeled off the backing paper 48 and placed on the bottle 12.

Figure 7:
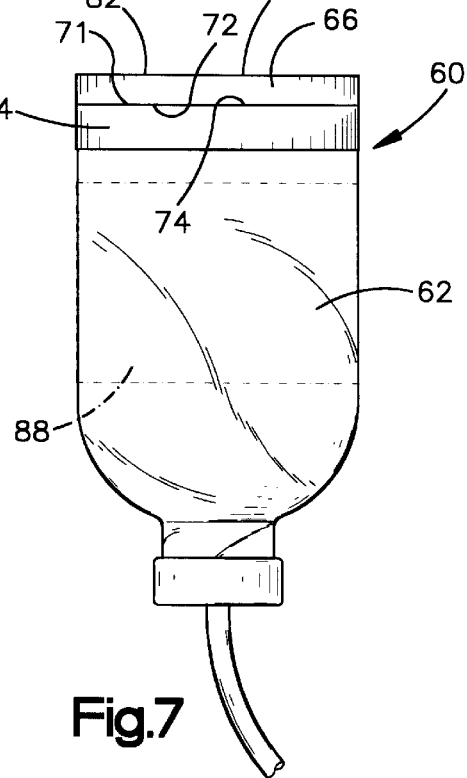
FIG. 7 is a plan view of the hanger of FIG. 6 attached to a bottles.

A second embodiment of the present invention includes a hanger 60 (FIG. 7), made of a single piece of film, attached to a bottle 62. The hanger 60 includes an attaching portion 64 encircling a portion of the bottle 62. The attaching portion 64 has an adhesive for attaching the hanger 60 to the bottle 62. A hanger portion 66 is movable from a first position in which the hanger portion also encircles a portion of the bottle 62 (FIG. 7) to a second position in which the hanger portion is spaced from the bottle and engageable with the hook 14.

The hanger portion 66 has a first end portion 68 and a second end portion 70. The first and second end portions 68 and 70 are connected to the attaching portion 64. The first and second end portions 68 and 70 are located on opposite sides of the bottle 62 so that the hanger portion 66 encircles approximately one-half of the bottle.

Figure 6:
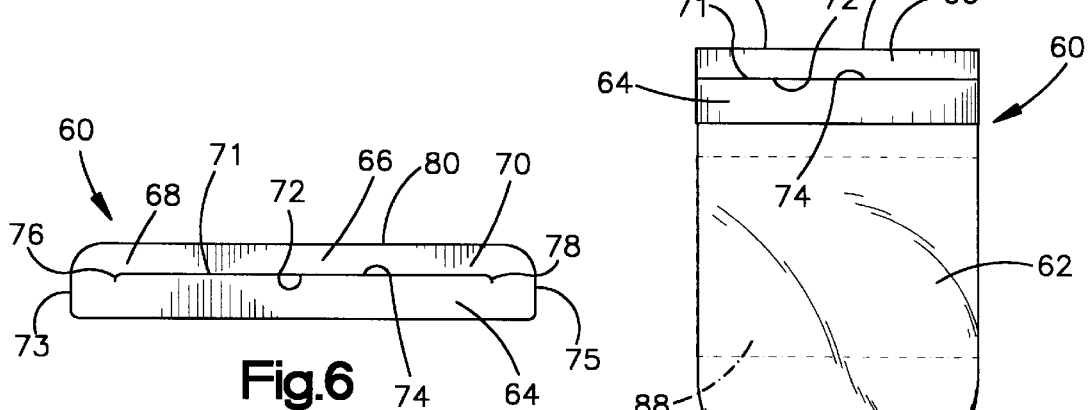
FIG. 6 is a plan view of a second embodiment of a hanger embodying the present invention.

The hanger portion 66 is formed by a linear die-cut 71. The hanger portion 66 has a linear edge 72 extending between the first end portion 68 and the second end portion 70 (FIG. 6). The linear edge 72 extends between edges 73 and 75 of the attaching portion 64 and has a length greater than one-half the distance between the edges 73 and 75 measured along the linear edge 72. The linear edge 72 extends parallel to a linear edge 74 of the attaching portion 64 when the hanger portion 66 is in the position shown in FIG. 7. The die-cut 71 has curved portions 76 and 78 adjacent end portions 68 and 70, respectively, for stress relief. The hanger portion 66 has a terminal edge 80 extending parallel to the linear edge 72 and lying adjacent to a base 82 of the bottle 62 when the hanger portion is in the position shown in FIG. 7. Preferably, the terminal edge 80 lies in the plane of the base 82 of the bottle 62.

The hanger portion 66 includes a surface extending from the first end portion 68 to the second end portion 70. The surface encircles a portion of the bottle 62 and faces the bottle when the hanger portion 66 is in the position shown in FIG. 7. The surface is engageable with the hook 14 when the hanger portion 66 is spaced from the attaching portion 64 and the bottle 62. The surface has a substantially arcuate shape and faces the bottle 62 along the entire length of the surface when the hanger portion 66 hangs the bottle from the hook 14.

The bottle 62 may have a label 88 separate from the hanger 60. The label 88 would have information about the contents of the bottle 62. It is also contemplated that a plurality of hangers 60 may be supplied on a roll. The hangers 60 can be peeled off backing paper and placed on the bottle 62.

Figures 8, 9:
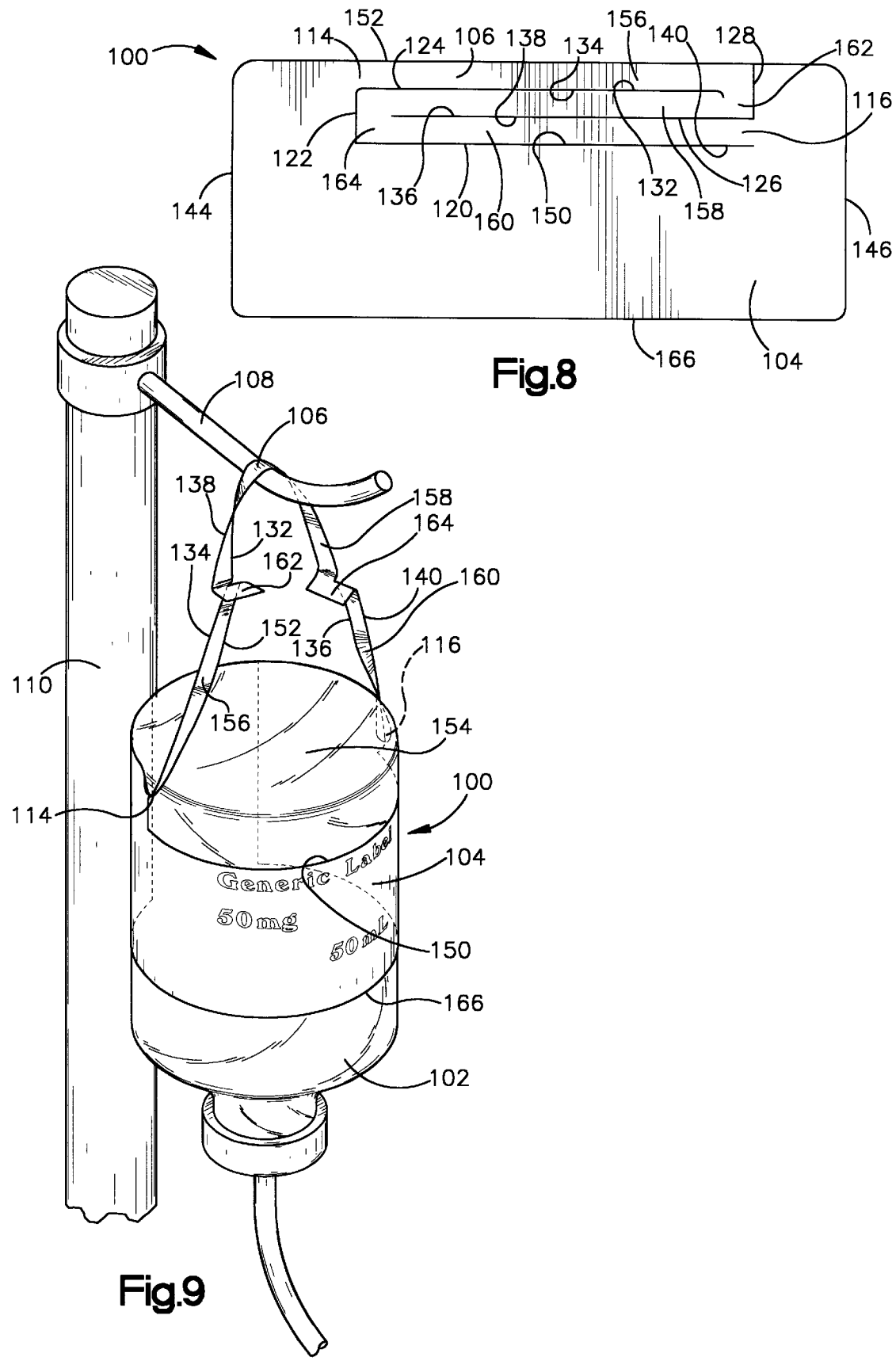
FIG. 8 is a plan view of a third embodiment of a hanger embodying the present invention.
FIG. 9 is a pictorial view of an intravenous feeding bottle with the hanger of FIG. 8 attached to the bottle.

A third embodiment of the present invention includes a hanger 100 (FIGS. 8 and 9), made of a single piece of film attached to a bottle 102. The hanger 100 includes an attaching portion 104 encircling a portion of the bottle 102. The attaching portion 104 has an adhesive for attaching the hanger 100 to the bottle 102. The attaching portion 104 may have information about the contents of the bottle printed on it, in which case, the hanger 100 would be a label. A hanger portion 106 is movable from a first position in which the hanger portion encircles approximately half the circumference of the bottle 102 to a second position in which the hanger portion is spaced from the bottle and engageable with a hook 108 of an intravenous stand 110 (FIG. 9).

The hanger portion 106 has a first end portion 114 and a second end portion 116. The first and second end portions 114 and 116 are connected to the attaching portion 104. The hanger portion 106 is formed by linear die cuts 120, 122, 124, 126 and 128. The linear die cut 122 extends perpendicular to and intersects linear die cuts 120 and 124. The linear die cut 128 extends perpendicular to and intersects the linear die cut 126.

The hanger portion 106 has a plurality of linear edges 132, 134, 136, 138, and 140. Each of the linear edges 132, 134, 136, 138, and 140 extends between edges 144 and 146 of the attaching portion 104 and has a length greater than one-half the distance between the edges 144 and 146 measured along each of the linear edges. The linear edges 132, 134, 136, 138, and 140 extend parallel to each other and a linear edge 150 of the attaching portion 104 when the hanger portion 106 is in the position shown in FIG. 8. The hanger portion 106 has a terminal edge 152 extending parallel to the linear edges 132, 134, 136, 138, and 140 and lying adjacent to a base 154 of the bottle 102 when the hanger 100 is attached to the bottle and the bottle is not hanging from the hook 108. Preferably, the terminal edge 152 lies in the plane of the base 154 of the bottle 102.

The die-cuts 122, 124, 126, and 128 define portions 156, 158, and 160 of the hanger portion 106. The portions 156, 158, and 160 extend parallel to each other when in the position shown in FIG. 8. When the hanger portion 106 is in the position shown in FIG. 9, the portion 158 of the hanger portion 106 engages the hook. The portion 156 extends from the end portion 114 of the hanger portion 106 to a first intermediate portion 162. The portion 158 extends from the first intermediate portion 162 to a second intermediate portion 164. The portion 160 extends from the second intermediate portion 164 to the second end portion 116 of the hanger portion 106. The portion 156 includes the terminal edge 152 and the edge 134. The portion 158 includes the edges 132 and 138. The portion 160 includes the edges 136 and 140.

The attaching portion 104 has an edge 166 (FIG. 8) extending parallel to the edges 132, 134, 136, 138, 140, 150, and 152. The edges 144 and 146 of the attaching portion 104 extend parallel to each other and perpendicular to the edges 132, 134, 136, 138, 148, 150, 152, and 166. Accordingly, the hanger 100 has a generally rectangular shape.

It is contemplated that a plurality of hangers 100 may be supplied on a roll. The hangers 100 can be peeled off backing paper and placed on a bottle 102.

The hanger of the present invention may have further alternative constructions. For example, the edges 30, 32 of the attaching portion 18 and hanger portion 22 could be connected by a small nib in a small area where the die cut is interrupted. The nib would break when the hanger portion 22 is moved to the position shown in FIG. 1. Also, the edges 35, 37, 38, 39 can be shaped, particularly at the corners, to give the hanger a desired appearance. Further, the hanger could have multi-layers with one layer having a release coating as in U.S. Pat. No. 5,135,125 in which case the die cut would not have to go through the thickness of the entire label, but rather only to the release coating. In this case, the hanger portion 22 would separate from a portion of the hanger 10 located between the bottle and the hanger portion 22 when the hanger portion 22 is moved to the position of FIG. 1.

From the above description of the invention, those skilled in the art will perceive improvements, changes and modifications. Such improvements, changes and modifications within the skill of the art are intended to be covered by the appended claims.

Having described the invention, the following is claimed:

1. A hanger for hanging an intravenous feeding bottle having a bottom from a hook, said hanger comprising:
    an attaching portion adapted to encircle and be attached to a portion of the bottle to attach said hanger to the bottle;
    a hanger portion movable relative to said attaching portion from a first position in which said hanger portion is adapted to encircle a portion of the bottle to a second position in which said hanger portion is adapted to engage the hook;
    said hanger portion and said attaching portion being portions of a single piece of film;
    said hanger portion having first and second end portions connected to said attaching portion;
    said hanger portion consisting essentially of a single strip of said film, said strip having first and second edges and being located at a terminal first end of said attaching portion when in said first position, said strip being movable from said first position to said second position by initially moving from said first position along said portion of the bottle and thereafter moving over the bottom of the bottle.

2. A hanger as set forth in claim 1 wherein said attaching portion is a label including information about the contents of the bottle.

3. A hanger as set forth in claim 1 wherein said hanger portion consists essentially of a single linearly extending strip.

4. A hanger as defined in claim 1 wherein said first and second edges of said hanger portion extend parallel to each other.

5. A hanger as defined in claim 4 wherein said attachment portion has a terminal second end opposite said first end, said terminal second end having a terminal edge extending parallel to said first and second edges of said hanger portion.

6. A hanger as defined in claim 1 wherein said attachment portion has a terminal second end opposite said first end, said terminal second end having a terminal edge extending parallel to said first and second edges of said hanger portion.

7. A hanger for hanging an intravenous feeding bottle having a bottom on a hook, said hanger comprising:
    an attaching portion adapted to encircle a portion of the bottle and having means for attaching said hanger to the bottle, said attaching portion having first and second edges; and
    a hanger portion movable relative to said attaching portion from a first position in which said hanger portion is adapted to encircle a portion of the bottle to a second position in which said hanger portion is adapted to engage the hook;
    said hanger portion and said attaching portion being portions of a single piece of film;
    said hanger portion having first and second end portions connected to said attaching portion and a third edge lying between said first and second edges of said attaching portion, said third edge extending between said first and second end portions connected to said attaching portion;
    said hanger portion comprising a single strip of said film, said strip being located at a terminal first end of said attaching portion when in said first position, said strip being movable from said first position to said second position by initially moving from said first position along said portion of said bottle and thereafter moving over the bottom of the bottle.

8. A hanger as set forth in claim 7 wherein said hanger portion has a terminal edge extending parallel to said third edge, said terminal edge adapted to lie adjacent to the bottom of the bottle when said hanger portion is in said first position.

9. A hanger as set forth in claim 8 wherein said attaching portion is a label including information about the contents of the bottle.

10. A hanger as set forth in claim 7 wherein said hanger portion includes a surface extending from said first end portion to said second end portion, said surface adapted to face the bottle when said hanger portion is in said first position and adapted to engage with the hook when said hanger portion is in said second position.

11. A hanger as set forth in claim 7 wherein said third edge is a linear edge and said hanger portion is a single linearly extending strip.

* * * * *